United States Patent [19]
Cohen

[11] Patent Number: 6,106,481
[45] Date of Patent: Aug. 22, 2000

[54] METHOD AND APPARATUS FOR ENHANCING PATIENT COMPLIANCE DURING INSPIRATION MEASUREMENTS

[75] Inventor: Alan M. Cohen, Arlington, Mass.

[73] Assignee: Boston Medical Technologies, Inc., Wakefield, Mass.

[21] Appl. No.: 08/942,710

[22] Filed: Oct. 1, 1997

[51] Int. Cl.$^7$ .................................................. A61N 5/00
[52] U.S. Cl. ......................... 600/534; 600/538; 128/898
[58] Field of Search .......................... 600/500, 528–538; 128/900–925, 897–899

[56] References Cited

U.S. PATENT DOCUMENTS

| | | |
|---|---|---|
| 2,649,573 | 8/1953 | Goldberg et al. . |
| 3,142,796 | 7/1964 | Goldberg et al. . |
| 3,340,867 | 9/1967 | Kubicek et al. . |
| 3,407,818 | 10/1968 | Costanzo . |
| 3,560,845 | 2/1971 | Goldberg et al. . |
| 3,731,184 | 5/1973 | Goldberg et al. ..................... 324/34 R |
| 3,925,762 | 12/1975 | Heitlinger et al. ..................... 340/150 |
| 3,991,304 | 11/1976 | Hillsman ............................ 235/151.34 |
| 4,023,563 | 5/1977 | Reynolds et al. .................. 128/2.05 R |
| 4,031,885 | 6/1977 | Davis et al. ........................... 128/2.08 |

(List continued on next page.)

FOREIGN PATENT DOCUMENTS

| | | |
|---|---|---|
| 2113101 | 3/1983 | United Kingdom .......... A61M 16/00 |
| WO 97/12546 | 10/1997 | WIPO . |

OTHER PUBLICATIONS

"Inductive plethysmography—a new repiratory transducer", J.S. Mullbridge and F.D. Scott, Proceedings of the Physiological Society, Jan. 1997, pp. 4P–5P.

Primary Examiner—Cary O'Connor
Assistant Examiner—Michael Astorino
Attorney, Agent, or Firm—Daly, Crowley & Mofford, LLP

[57] ABSTRACT

A system for measuring a patient's inspiration volume and for enhancing patient compliance with a predetermined breathing pattern during inspiration volume measurements. A flexible conductive loop adapted for being wrapped around, and conforming to the patient's chest is coupled to an amplifier circuit including a signal generator and an exclusive-OR gate. The signal generator generates a square-wave signal for coupling to a first terminal of the conductive loop and the exclusive-OR gate is responsive to the applied square-wave signal and to a signal at the second terminal of the loop for measuring the delay between the signals. The output signal of the amplifier circuit is indicative of the inductance of the loop, which varies with the patient's inspiration volume. The measured inspiration volume is displayed on a first display and a target inspiration volume is displayed on a second display, preferably, disposed adjacent to the first display. The patient is instructed to breathe in a manner that causes the measured inspiration volume display to match the target inspiration volume display. In one embodiment, a measure of the patient's compliance with the predetermined breathing pattern is provided.

14 Claims, 9 Drawing Sheets

6,106,481
Page 2

U.S. PATENT DOCUMENTS

| | | | |
|---|---|---|---|
| 4,036,215 | 7/1977 | Doll | 128/2.05 F |
| 4,137,910 | 2/1979 | Murphy | 128/2.05 R |
| 4,216,779 | 8/1980 | Squires et al. | 128/682 |
| 4,240,442 | 12/1980 | Andresen et al. | 128/708 |
| 4,308,872 | 1/1982 | Watson et al. | 128/725 |
| 4,346,718 | 8/1982 | Morris | 128/710 |
| 4,364,397 | 12/1982 | Citron et al. | 128/710 |
| 4,367,753 | 1/1983 | Jirak . | |
| 4,408,614 | 10/1983 | Weaver et al. | 128/680 |
| 4,433,693 | 2/1984 | Hochstein | 128/721 |
| 4,440,177 | 4/1984 | Anderson et al. | 128/719 |
| 4,446,872 | 5/1984 | Marsoner et al. | 128/700 |
| 4,506,678 | 3/1985 | Russell et al. | 128/723 |
| 4,513,295 | 4/1985 | Jones et al. | 346/33 ME |
| 4,559,947 | 12/1985 | Renger et al. | 128/419 PG |
| 4,649,929 | 3/1987 | Weaver et al. | 128/680 |
| 4,679,144 | 7/1987 | Cox et al. | 364/417 |
| 4,692,148 | 9/1987 | Kantrowitz et al. | 604/96 |
| 4,721,114 | 1/1988 | DuFault et al. | 128/696 |
| 4,777,960 | 10/1988 | Berger et al. | 128/706 |
| 4,807,640 | 2/1989 | Watson et al. | 128/721 |
| 4,815,473 | 3/1989 | Watson et al. | 128/721 |
| 4,819,654 | 4/1989 | Weaver et al. | 128/680 |
| 4,832,038 | 5/1989 | Arai et al. | 128/670 |
| 4,862,361 | 8/1989 | Gordon et al. | 364/413.06 |
| 4,869,262 | 9/1989 | Orr et al. | 128/672 |
| 4,870,974 | 10/1989 | Wang | 128/700 |
| 4,889,131 | 12/1989 | Salem et al. | 128/671 |
| 4,905,708 | 3/1990 | Davies | 128/705 |
| 4,909,260 | 3/1990 | Salem et al. | 128/721 |
| 4,913,146 | 4/1990 | DeCote, Jr. | 128/419 PG |
| 4,930,517 | 6/1990 | Cohen et al. | 128/671 |
| 4,934,377 | 6/1990 | Bova et al. | 128/696 |
| 4,947,857 | 8/1990 | Albert et al. | 128/696 |
| 4,979,110 | 12/1990 | Albrecht et al. | 364/413.03 |
| 4,984,158 | 1/1991 | Hillsman | 364/413.04 |
| 5,025,794 | 6/1991 | Albert et al. | 128/696 |
| 5,027,824 | 7/1991 | Dougherty et al. | 128/702 |
| 5,148,812 | 9/1992 | Verrier et al. | 128/704 |
| 5,156,148 | 10/1992 | Cohen | 128/419 PG |
| 5,159,935 | 11/1992 | Sackner et al. | 128/721 |
| 5,167,506 | 12/1992 | Kilis et al. | 434/262 |
| 5,269,301 | 12/1993 | Cohen | 607/6 |
| 5,277,189 | 1/1994 | Jacobs | 128/696 |
| 5,285,793 | 2/1994 | Slovut et al. | 128/706 |
| 5,299,119 | 3/1994 | Kraf et al. | 364/413.06 |
| 5,301,678 | 4/1994 | Watson et al. | 128/721 |
| 5,312,441 | 5/1994 | Mader et al. | 607/5 |
| 5,316,008 | 5/1994 | Suga et al. | 128/700 |
| 5,330,508 | 7/1994 | Gunderson | 607/14 |
| 5,333,106 | 7/1994 | Lanpher et al. | 364/413.01 |
| 5,360,008 | 11/1994 | Campbell, Jr. | 128/671 |
| 5,390,679 | 2/1995 | Martin | 128/673 |
| 5,394,873 | 3/1995 | Kraemer et al. | 128/653.2 |
| 5,400,795 | 3/1995 | Murphy et al. | 128/702 |
| 5,423,325 | 6/1995 | Burton | 128/702 |
| 5,437,285 | 8/1995 | Verrier et al. | 128/702 |
| 5,450,850 | 9/1995 | Iinuma | 128/661.09 |
| 5,483,969 | 1/1996 | Testerman et al. | 600/529 |
| 5,485,847 | 1/1996 | Baker, Jr. | 128/666 |
| 5,497,778 | 3/1996 | Hon | 128/672 |
| 5,509,404 | 4/1996 | Lloyd et al. | 128/200.14 |
| 5,520,190 | 5/1996 | Benedict et al. | 128/700 |
| 5,543,012 | 8/1996 | Watson et al. | 156/440 |
| 5,546,952 | 8/1996 | Erickson | 600/529 |
| 5,582,182 | 12/1996 | Hillsman | 128/716 |
| 5,627,327 | 5/1997 | Zanakis | 73/862.042 |
| 5,724,580 | 3/1998 | Levin et al. | 395/615 |

METHOD AND APPARATUS FOR ENHANCING PATIENT COMPLIANCE DURING INSPIRATION MEASUREMENTS

CROSS-REFERENCE TO RELATED APPLICATIONS

Not applicable.

STATEMENTS REGARDING FEDERALLY SPONSORED RESEARCH

Not applicable.

BACKGROUND OF THE INVENTION

Various medical diagnostic apparatus require that aspects of a patient's respiration, such as inspiration volume, be measured. Illustrative of such apparatus are heart rate variability assessment monitors which can be used in the diagnosis and treatment of various disease states.

Conventional inspiration volume measurement techniques have required the use of face masks or mouthpieces which are invasive and often uncomfortable. One noninvasive technique for measuring a patient's inspiration volume utilizes an extensible conductor adapted for wrapping around the patient's chest in the form of a loop. The conductor is connected to an electrical circuit with which its inductance is measured. One such circuit is described in U.S. Pat. Nos. 4,815,473 and 4,308,872 of Respitrace Corporation, in which the conductive loop provides the inductor in an LC oscillator circuit. The LC oscillator circuit generates a signal having a frequency which varies in accordance with the inductance of the loop. Since the loop inductance varies with variations in the cross-sectional area encompassed by the loop which, in turn, varies with the patient's inspiration volume, the frequency of the oscillator signal varies with the patient's inspiration volume. The frequency signal is converted into a voltage signal having an amplitude proportional to the loop inductance and thus, to the patient's inspiration volume.

While the circuit described in the '473 and '872 patents overcomes drawbacks associated with conventional invasive inspiration volume measurement techniques, the measurement accuracy of the circuit may be limited. This is because the output signal of the circuit is not consistently linearly related to the patient's inspiration volume. A further drawback of the circuit disclosed in these patents is the relatively large number of components required, which lessens its desirability due to manufacturing and cost considerations.

In certain applications, it is advantageous to have the patient breathe in a particular manner when measuring inspiration volume. As one example, in neuropathy diagnosis, it is desirable that the patient breathe at a predetermined, constant frequency, such as on the order of six breaths/minute, or 0.10 Hz. However, even with specific instructions, it is difficult to ensure that the patient will breathe at the constant, predetermined frequency (i.e., to ensure "patient compliance" with a desired breathing pattern). Further, even if the patient complies closely with the desired breathing pattern, a patient's breathing often varies between tests, rendering the results of long-term testing less meaningful due to inter-test variability.

In an effort to enhance patient compliance and thus to reduce inter-test variability, some conventional systems include interactive mechanisms by which the patient is instructed to breathe in accordance with a particular pattern. For example, in a cardiac risk assessment monitor sold under the product name HRView™ versions I and II by Boston Medical Technologies, Inc., different audio tones are used to indicate to the patient when to inhale and when to exhale. While this arrangement improves patient compliance and reduces inter-test variability, an even more effective way of ensuring patient compliance with a particular breathing pattern is desirable.

BRIEF SUMMARY OF THE INVENTION

Apparatus and methods for accurately measuring a patient's inspiration volume are disclosed. The apparatus is advantageously simple and relatively inexpensive and utilizes a flexible conductive loop adapted for being wrapped around, and conforming to the patient's chest. An amplifier circuit coupled to the conductive loop includes a signal generator for applying a square-wave signal to a first terminal of the loop and circuitry for measuring the delay between the applied square-wave signal and a pseudo-square-wave signal at the second terminal of the loop. The pseudo-square-wave signal has rounded edges relative to the applied square-wave signal. Preferably, the pseudo-square-wave signal is processed by a comparator which converts the signal into a delayed square-wave signal for measurement of the delay between the applied square-wave signal and the delayed square-wave signal. The measured delay varies with variations in the inductance of the conductive loop and thus, with the patient's inspiration volume.

In one embodiment, the delay measuring circuit includes an exclusive-OR gate having a first input terminal responsive to the applied square-wave signal and a second input terminal responsive to the delayed square-wave signal. The digital output signal of the exclusive-OR gate transitions to a logic high level when the applied square-wave signal goes high and transitions to a logic low level when the delayed square-wave signal goes high. The output signal of the exclusive-OR gate is filtered by a low pass filter and is further processed by reducing or removing any DC offset and preferably, also by increasing the gain to provide an amplified output signal indicative of the patient's inspiration volume.

In accordance with a further aspect of the invention, the inspiration volume measurement apparatus is provided in a system which enhances patient compliance with a predetermined breathing pattern. The system includes a first display on which the patient's measured inspiration volume is displayed, a second display on which a target inspiration volume is displayed and a processor for controlling the first and second displays. The processor is operative to control the first display in response to a digital version of the amplified output signal and to control the second display in accordance with a predetermined function, such as a sine wave function. The patient is instructed to breathe so as to cause the measured inspiration volume display to match the target inspiration volume display.

Preferably, each of the first and second displays comprises a corresponding plurality of display elements disposed adjacent to one another in order to facilitate visual comparison. In one embodiment, the display elements are LEDs arranged in the form of bar graphs. A demultiplexer associated with each display is responsive to common data input signals and a respective strobe signal provided by the processor for generating a plurality of output signals for driving the display elements. The strobe signals control the latching of the data input signals by the respective demultiplexer.

Also described is a method for enhancing patient compliance with a predetermined breathing pattern including the steps of measuring the patient's inspiration volume, displaying the measured inspiration volume, displaying a target inspiration volume in accordance with a predetermined function, such as a sine wave function, and instructing the patient to breathe in a manner that causes the measured inspiration volume display to match the target inspiration volume display. In one embodiment, the method includes the further step of providing an indication of the extent to which the measured inspiration volume matches the target inspiration volume, such as by performing a frequency analysis on the measured inspiration volume signal to determine the signal power at a predetermined frequency.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Figure 1:
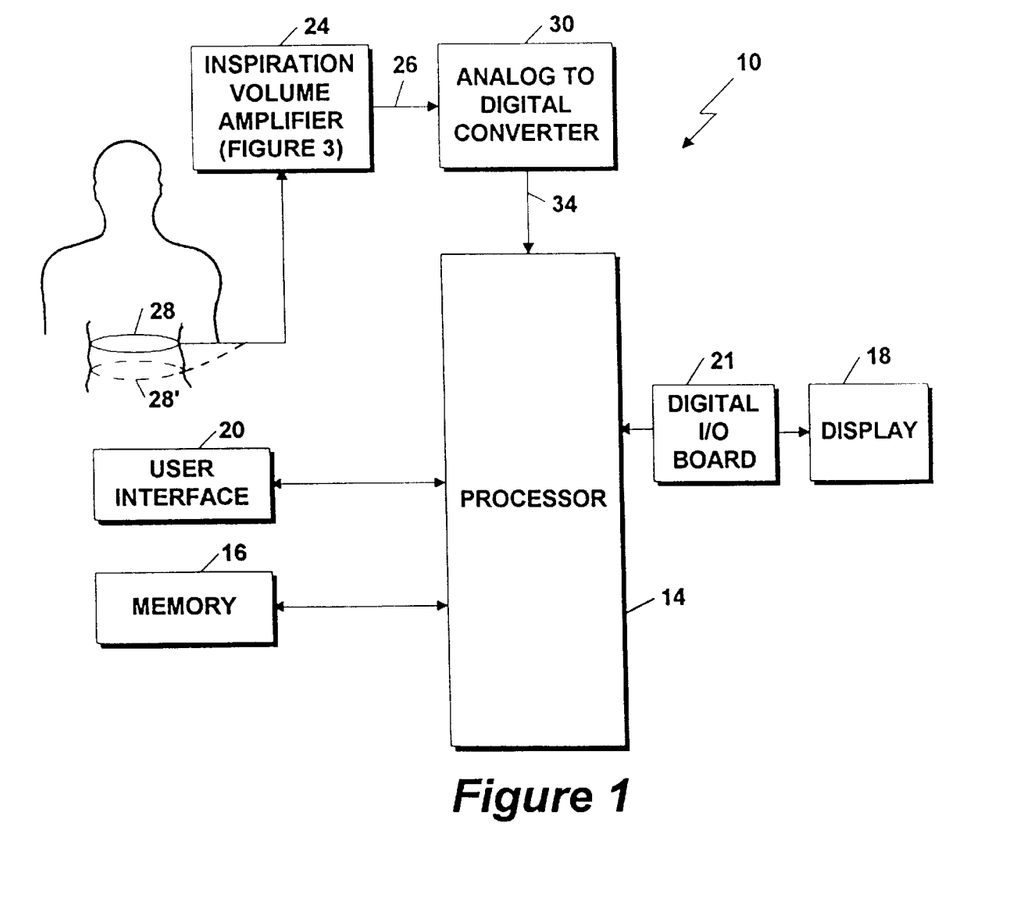
FIG. 1 is a block diagram of a medical diagnostic system including apparatus for measuring inspiration volume and for enhancing patient compliance with a predetermined breathing pattern.

Referring to FIG. 1, a medical diagnostic system 10 includes apparatus and implements techniques for measuring and displaying a patient's inspiration volume. The system 10 may be one of various types of medical diagnostic apparatus in which it is desired to measure a patient's inspiration volume.

The system 10 further includes apparatus and implements techniques for improving patient compliance with performance of a desired task during measurements, such as breathing in a predetermined pattern during inspiration volume measurements. It will be appreciated by those of ordinary skill in the art that the apparatus and techniques described herein are suitable for enhancing patient compliance with performance of a desired task during various types of measurements. However, for simplicity of illustration, the system is described with particular reference to enhancing patient compliance with a predetermined breathing pattern during inspiration volume measurements.

The system 10 includes a processor 14 in electrical communication with a memory 16, a display 18 and a user interface 20. An inspiration volume amplifier circuit 24 is coupled to a patient interface 28 and includes circuitry for measuring the inductance of the patient interface to provide an analog amplifier output signal 26 indicative of the patient's instantaneous inspiration volume. The amplifier output signal 26 is coupled to an analog-to-digital converter 30 for conversion into a digital signal 34 indicative of the patient's instantaneous inspiration volume which is coupled to the processor 14, as shown.

The patient interface 28 is provided in the form of a flexible conductor, or conductive loop, suitable for wrapping around and conforming to the patient's chest in an extensible manner (i.e., by expanding and contracting as the patient inhales and exhales, respectively). Various forms of the conductive loop 28 are suitable, such as a wire sewn into a flexible elastic belt which permits the wire to conform to the patient's body. Further suitable forms of the conductive loop 28 are shown and described in U.S. Pat. Nos. 4,815,473, 4,308,872, 4,807,640, 5,301,678 and 5,543,012, each of which is incorporated herein by reference. One suitable commercially available conductive loop is sold by Ambulatory Monitoring, Inc. of Ardsley, N.Y. under the product name RESPIBAND.

In certain cases, it may be desirable to utilize a plurality of loops (i.e., illustrated by loops 28 and 28') adapted for being disposed around and conforming to different regions of the patient's chest or torso. In such applications, the loops are coupled in series in the amplifier circuit 24 of FIG. 3. The sum of the inductance of such series-coupled loops provides an indication of the change in the patient's inspiration volume.

The processor 14 stores the digital inspiration volume signal 34 in memory 16 and displays the measured inspiration volume on the display 18. To this end, the processor 14 is coupled to the display 18 via a digital Input/Output (I/O) card 21 which latches digital output signals from the processor 14 for coupling to the display 18. One suitable digital I/O card is of the type sold by Computerboards of Mansfield, Mass. More particularly, the measured inspiration volume is displayed on a first portion of the display 18. A target inspiration volume is generated by the processor 14 and displayed on a second portion of the display 18 in response to a predetermined function, such as a sine wave function. Preferably, the measured and target inspiration volume display portions are arranged to facilitate their comparison. In use, the patient, or subject, is instructed to breathe in a manner which causes the measured inspiration volume display portion to match the target inspiration volume display portion.

The processor 14 may take various forms, such as the microprocessor of a standard personal computer, workstation or other microprocessor-driven device. As one example, the processor 14 is an INTEL-compatible microprocessor of an IBM-compatible personal computer running the MICROSOFT WINDOWS graphical user interface. The memory 16 includes a Random Access Memory (RAM) and the user interface 20 may include a keyboard, touch screen and/or mouse. In the illustrative embodiment, the user interface 20 includes a touch screen incorporated into the display 18, the display is a flat panel LCD display of the type sold by Goldstar and the processor 14 and memory 16 are typical components associated with an IBM-compatible personal computer. The analog-to-digital converter 30 is a commercially available component, such as is sold by Computerboards of Mansfield, Mass. under the part number DAS1402/16. It will be appreciated by those of ordinary skill in the art, that the apparatus and techniques of the system 10 may be implemented on various equipment, both hardware and software.

Figure 2:
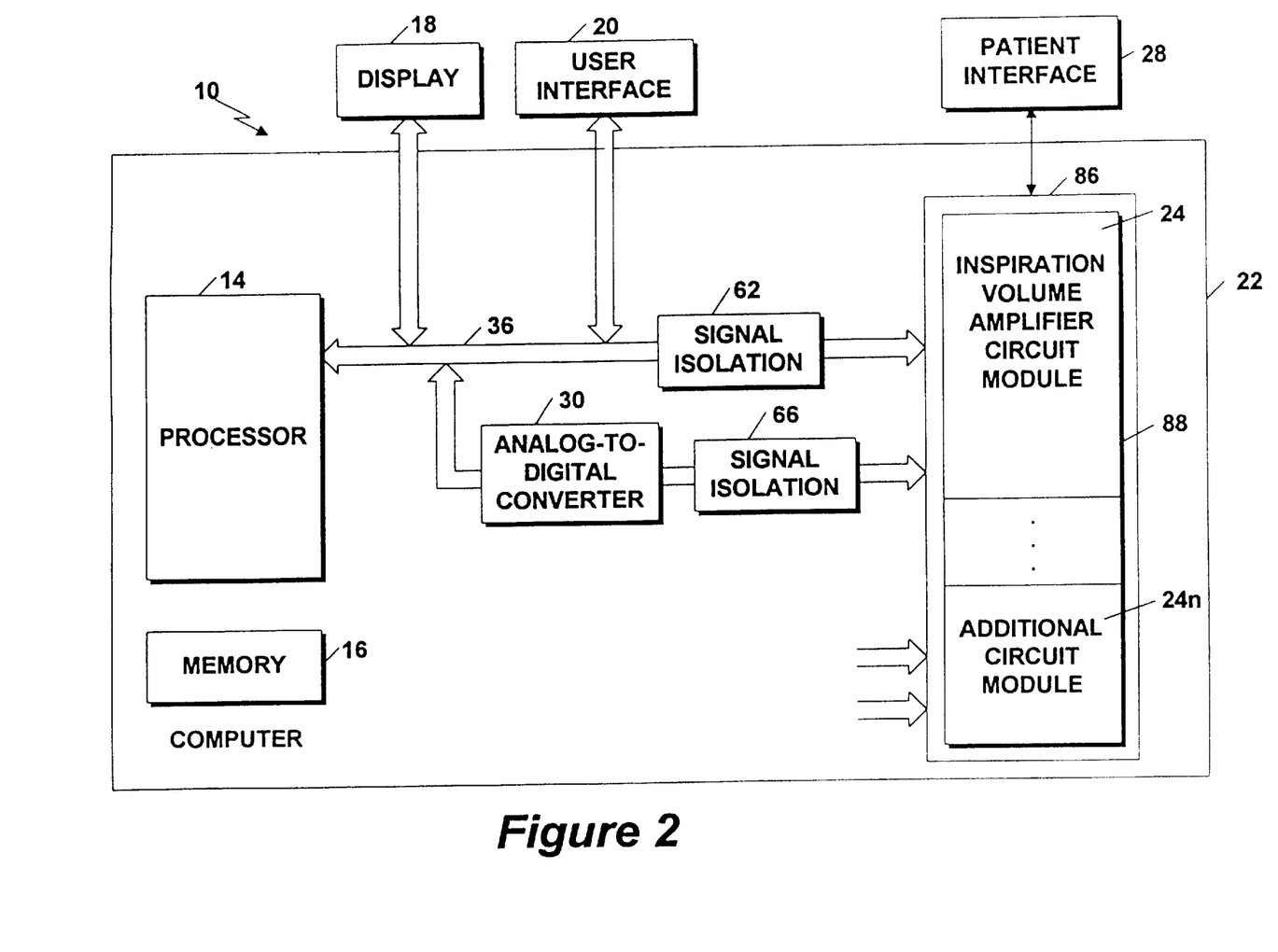
FIG. 2 is a block diagram of a computer-based implementation of the apparatus of FIG. 1.

Referring to FIG. 2, the inspiration volume amplifier 24 may be implemented in the form of a "circuit module" adapted for insertion into an Input/Output (I/O) port or slot 86 of a standard personal computer chassis 22. To this end, the circuit module 24 is housed in a metal or metallized-plastic box, or instrument chassis 88, which is adapted for insertion into an opening of the computer chassis 22 typically used for a diskette drive, tape drive or CD-ROM drive.

The system 10 may include additional circuitry (not shown) for measuring various other physiological signals of the patient, such as a blood pressure signal or an electrocardiogram signal, in which case such circuitry is implemented in the form of one or more additional circuit modules. The instrument chassis 88 has an open front face which permits insertion of one or more circuit module(s) therein. The front face of any unused portions of the instrument chassis is covered by metal or metallized panels. Advantageously, the instrument chassis serves as a "Gauss cage" to reduce electromagnetic interference (EMI).

With this arrangement, the processor 14 can communicate with and control the inspiration volume amplifier circuit module 24 via the computer's standard busses and the circuit module can draw on the power available to the computer components. The processor 14 transmits any control information to the circuit module 24 via the computer's digital control bus 36 and receives the digital version 34 of the analog amplifier output signal 26 via the computer's digital control bus 36. For safety reasons, it is preferable to isolate the computer bus 36 from the circuit module 24, for example, with the use of opto-isolators 62, 66, respectively.

Figure 3:
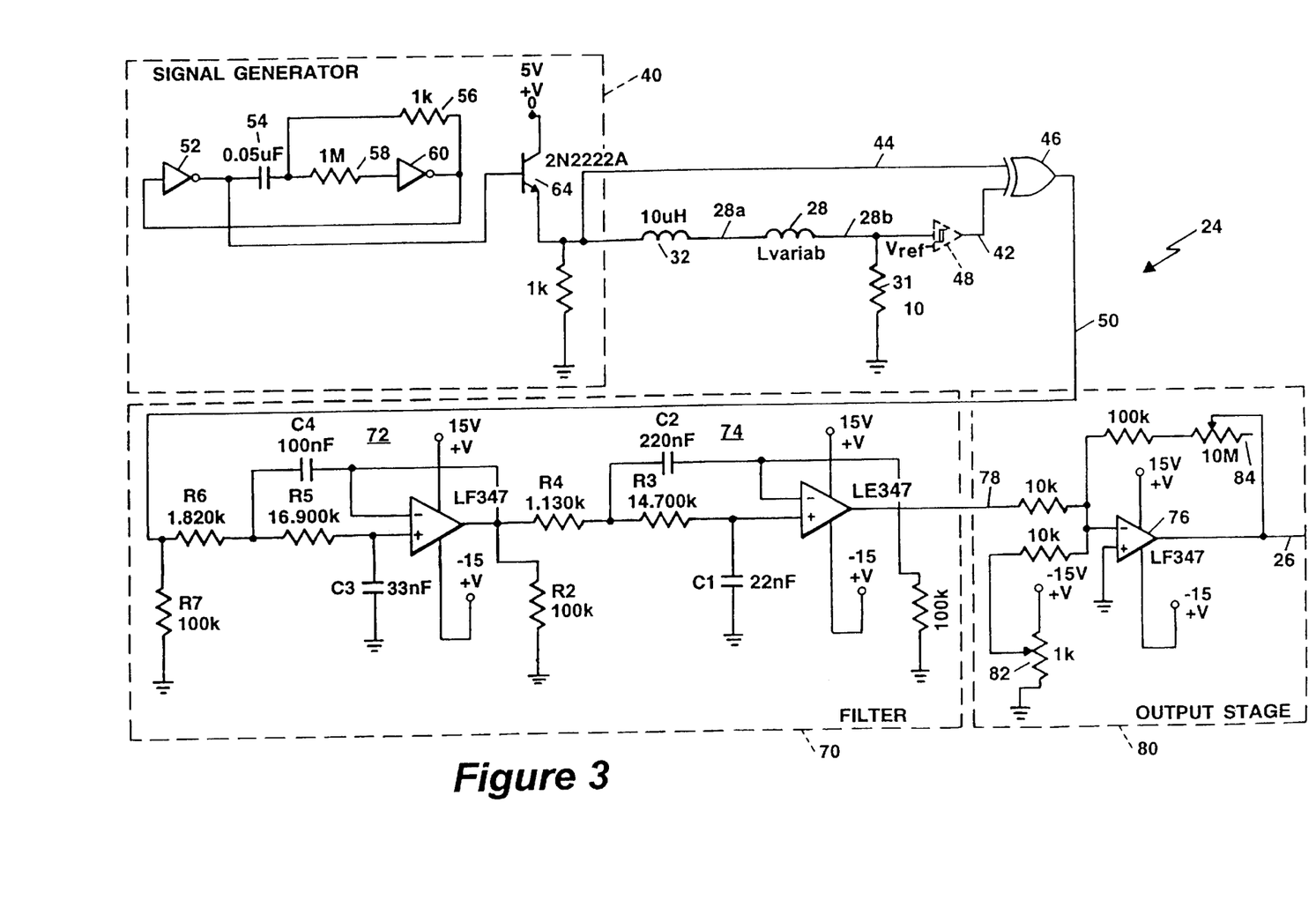
FIG. 3 is a schematic of the inspiration volume amplifier and patient interface of FIG. 1.

Referring to FIG. 3, the inspiration volume amplifier 24 is electrically connected to the conductive loop 28 (represented by the schematic symbol of an inductor). A signal generator 40 generates a square-wave signal 44 for coupling to first terminal 28a of the loop 28 via an inductor 32. A second terminal 28b of the loop 28 is coupled to a resistor 31, as shown.

Various circuitry is suitable for providing the signal generator 40. In the illustrative embodiment, the signal generator 40 is an oscillator circuit, including inverters 52, 60, a capacitor 54 and resistors 56, 58. The output of inverter 52 is coupled to the base of an npn transistor 64 having an emitter at which the square-wave signal 44 is provided. The transistor 64 provides current gain to the square-wave signal.

The inductance of inductor 32 and loop 28 has the effect of rounding the edges of the square-wave signal 44 to provide a pseudo-square-wave signal at the second terminal 28b of the inductor 28. Preferably, a comparator 48 is coupled to the second terminal 28b of the loop 28 as shown, in order to convert the pseudo-square-wave signal into a delayed square-wave signal 42. In the illustrative embodiment, the comparator 48 is provided with significant hysteresis, such as on the order of four volts. Use of the comparator 48 with hysteresis has the advantage of increasing noise immunity and providing an accurate and reliable threshold level Vref.

The amount of the delay between the square-wave signal 44 and the delayed square-wave signal 42 varies linearly with the variations in the inductance of loop 28. Stated differently, the signal at the second terminal 28b of the loop 28 is delayed as compared to the signal 44, with the amount of the delay being indicative of the inductance of loop 28 and thus, of the patient's instantaneous inspiration volume.

The inductor 32 is provided in order to increase the LC time constant between square-wave signal 44 and the pseudo-square-wave signal at loop terminal 28b. In the illustrative embodiment, inductor 32 is a 10 $\mu$H inductor and the conductive loop 28 has a nominal inductance of between approximately 3 $\mu$H and 5 $\mu$H. In use, the inductance of the loop 28 varies on the order of between 0.02 $\mu$H and 0.004 $\mu$H, depending on factors such as the size of the patient and the deepness of breathing. If the LC time constant is too small, then the delay between the square-wave signal 44 and the delayed square-wave signal 42 may be too small to measure accurately. Stated differently, the LC time constant needs to be at least as long as the time needed for the output of the comparator 48 and the exclusive-OR gate 46 to respond.

It will be appreciated by those of ordinary skill in the art that the delay between the square-wave signal 44 and the delayed square-wave signal 42 at the output of the comparator 48 can be measured using various circuitry and techniques. In the illustrative embodiment, an exclusive-OR gate 46 is provided for this purpose. A first input of the exclusive-OR gate 46 is responsive to the square-wave signal 44 and a second input is responsive to the delayed square-wave signal 42 at the output of the comparator 48.

Assuming that input signals 44 and 42 to the exclusive-OR gate 46 are initially at logic low levels, the output signal 50 of the exclusive-OR gate 46 transitions to a logic high level when the square-wave signal 44 goes high and transitions to a logic low level when the delayed square-wave signal 42 goes high. From the initial condition where both input signals 42, 44 to the exclusive-OR gate 46 are high, the output of the gate 46 goes high when the square-wave signal 44 goes low and goes low when the delayed square-wave signal 42 goes low. The output signal 50 thus has a duty cycle (i.e., ratio of the interval during which the signal is high to the total period) proportional to the delay between the signals 42 and 44 and thus, to the patient's inspiration volume.

Figure 3A:
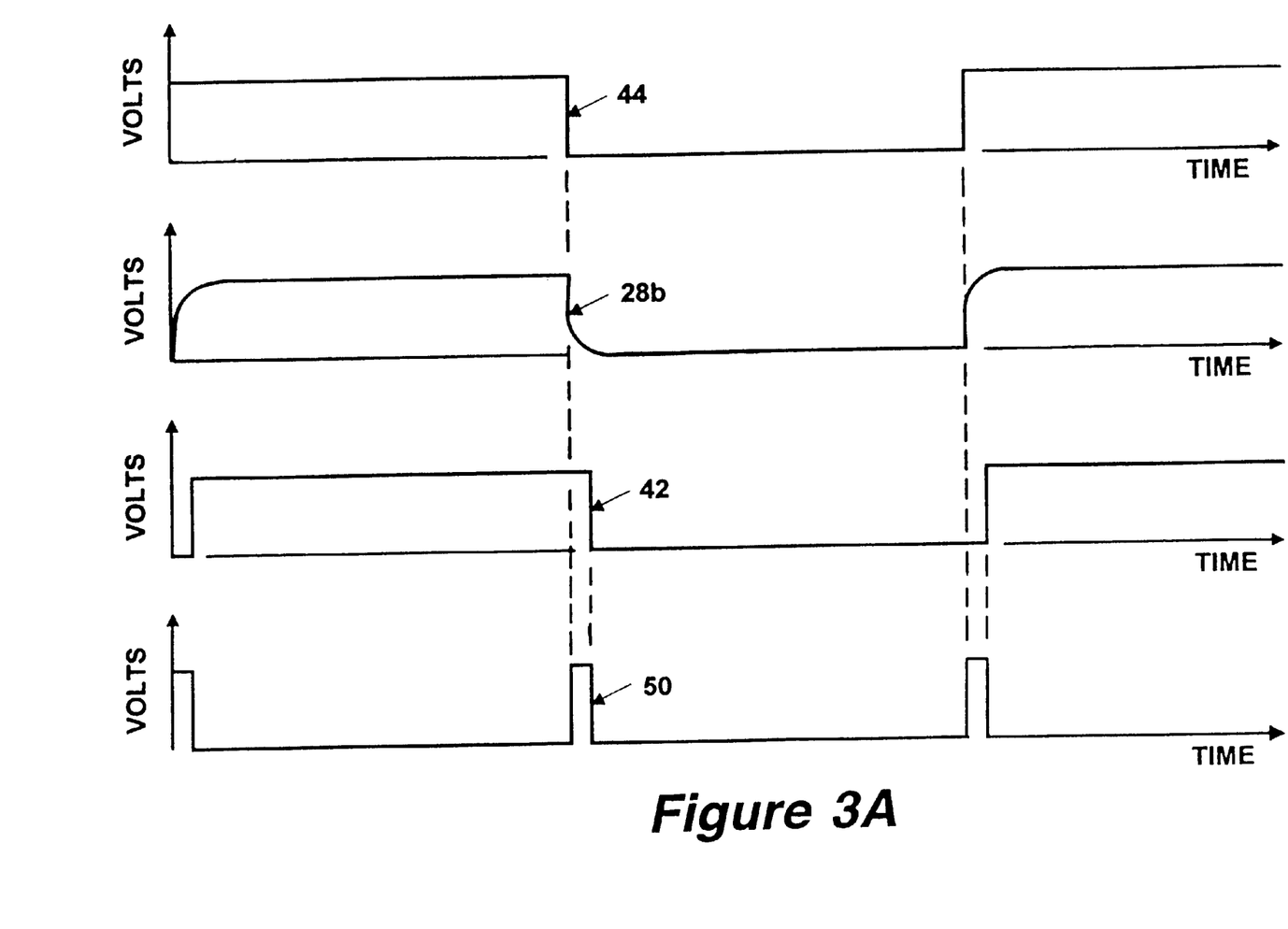
FIG. 3A shows various signal waveforms associated with the circuit of FIG. 3.

Referring also to FIG. 3A, the above-described operation of the exclusive-OR gate 46, as well as the relationship between various signals of circuit of FIG. 3 are illustrated. In particular, the signal waveforms shown in FIG. 3A include the square-wave signal 44, the pseudo-square-wave signal at terminal 28b, the output signal 42 of comparator 48 and the output signal 50 of the exclusive-OR gate 46, all drawn to the same time scale.

The output signal 50 of the exclusive-OR gate 46 is further processed by a filter 70 and an output stage 80. The filter 70 is a low pass filter which smooths the output signal 50 in order to facilitate measurement of the delay between the square-wave signal 44 and the delayed square-wave signal 42. In particular, the low pass filter 70 provides a low-frequency signal 78 having an amplitude proportional to the duty cycle of the signal 50. In the illustrative embodiment, filter 70 is a fourth-order low pass filter comprising two stages 72 and 74 and having a nominal cutoff frequency of approximately 350 Hz. In general, the cutoff frequency should be selected to be high enough so that the filter output signal 78 adequately responds to changes in the inductance of loop 28 and low enough to substantially reduce ripple at the frequency of the signal generator 40.

The filter output signal 78 is coupled to an operational amplifier 76 of the output stage 80. The output stage 80 includes an offset adjustment control 82 in the form of a potentiometer coupled to the inverting input of the amplifier 76. The potentiometer 82 is user-adjustable in order to reduce or remove the DC offset of the signal 78. This can be achieved by displaying the filtered signal 78 on the display 18, thereby enabling the user to adjust the potentiometer 82 until the DC offset is reduced or removed. Alternatively, an automated method for removing the DC offset may be implemented.

The output stage 80 further includes a gain adjustment control 84 in the form of a potentiometer coupled in feedback relationship with the operational amplifier 76, as shown. Since the amplitude of the digital output signal 50 is attenuated by the filter 70, it is generally desirable to increase the gain by adjusting the potentiometer 84. Preferably, the gain is selected so that the voltage difference in the amplifier output signal 26 between full exhalation and full inhalation by the patient is on the order of two volts centered within the supply voltage range (e.g., zero to five volts). In the illustrative embodiment, the potentiometer 84 is adjustable to vary the gain by a factor of between 10 and 1000. The output signal 26 of the amplifier is an analog signal having an amplitude that varies linearly with changes in the patient's inspiration volume.

Figure 4:
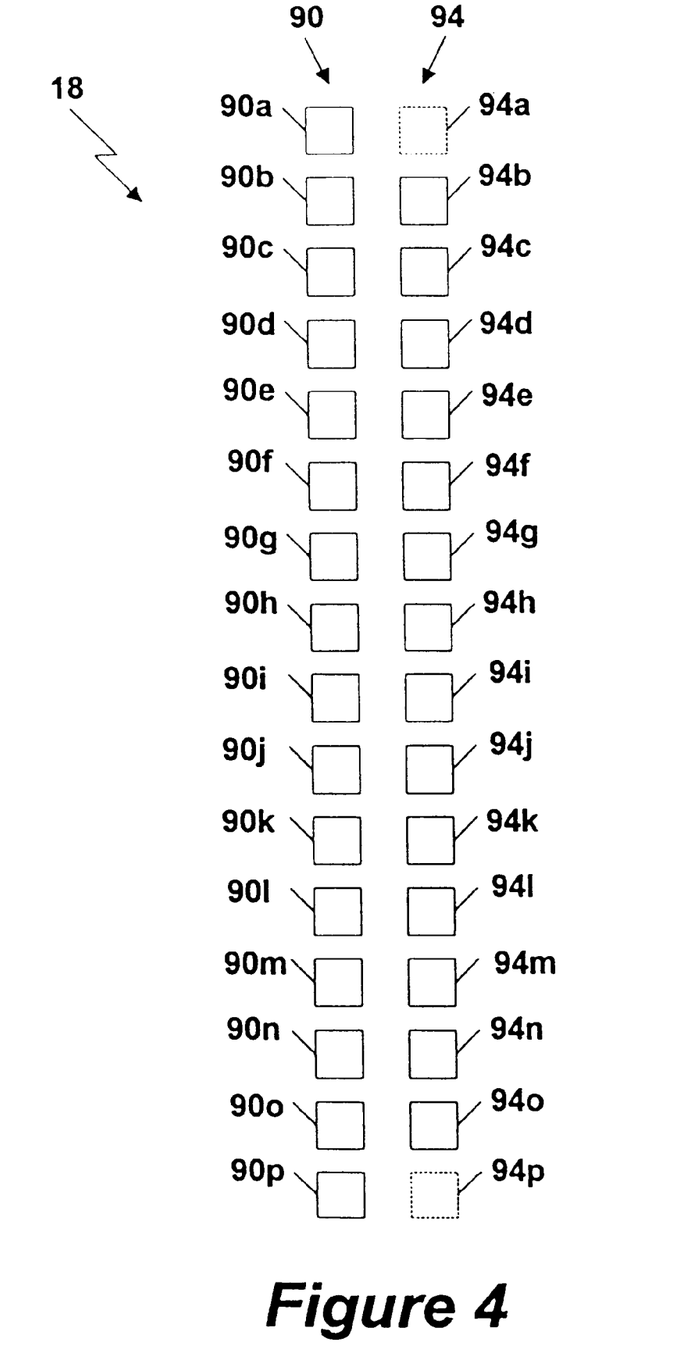
FIG. 4 illustrates the display of FIG. 1.

Referring to FIG. 4, the display 18 includes two portions 90 and 94. The first display portion 90 is used to display the patient's actual measured inspiration volume and the second display portion 94 is used to display a target, or desired inspiration volume to which the patient's breathing preferably conforms. In general, the target display portion 94 displays a predetermined breathing pattern including both an amplitude of inhalation and exhalation and a rate, or frequency. Preferably, the breathing pattern displayed on the target inspiration volume display follows a predetermined mathematical function, such as a sine wave function or a chirp function in which the frequency increases as a function of time. However, alternatively, the predetermined pattern may be a random pattern.

Each display portion 90, 94 includes a plurality of display elements 90a–90p, 94a–94p, respectively, and in the illustrative embodiment, includes sixteen light emitting diodes (LEDs). The LEDs of the display portions 90, 94 are arranged vertically in the form of bar graphs, as shown. Preferably, the display portions 90, 94 are disposed adjacent to one another in order to facilitate rapid visual comparison of the display elements, as will be described. It will be appreciated by those of ordinary skill in the art however, that various types of display elements and arrangements are possible and suitable in order to achieve the benefits described herein.

The bar graph display portions 90 and 94 are arranged such that illumination of each LED indicates a particular level, or range of lung volume. In the illustrative embodiment, the lowest LED corresponds to a greatest level of exhalation and the highest LED corresponds to a greatest level of inhalation. More particularly, with respect to the measured inspiration volume display portion 90, the lowest LED 90p indicates that the measured inspiration volume is less than a predetermined minimum level and the highest LED 90a indicates that the measured inspiration volume is greater than a predetermined maximum level.

The target display portion 94 is shown to include the same number of LEDs as the measured display portion 90, with each of the target LEDs 94a–94p disposed adjacent to, and preferably in substantial horizontal alignment with, a corresponding one of the LEDs 90a–90p of the measured inspiration volume display portion 90. However, since the uppermost measured inspiration volume LED 90a and the lowermost measured inspiration volume LED 90p indicate that the patient's inspiration volume is either greater than or less than predetermined maximum and minimum levels, respectively, the corresponding LEDs 94a, 94p of the target display portion 94 are not utilized since these are not desired conditions. However, LEDs 94a and 94p may be included since the bar graph display portions 90, 94 may be used display other information.

In operation, one of the LEDs in each of the display portions 90 and 94 is illuminated by the processor 14 at any given time. The illuminated one of the LEDs 94b–94o of the target display portion 94 indicates the desired level of inhalation or exhalation at the particular time; whereas, the illuminated one of the LEDs 90a–90p of the measured inspiration volume display portion 90 indicates the patient's present inspiration volume. The patient is instructed to breathe in a manner which causes the measured inspiration volume display portion 90 to illuminate the one of the LEDs 90b–90o which corresponds to, and preferably is horizontally aligned with, the illuminated one of the target LEDs 94b–94o. Stated differently, the patient is instructed to breathe so as to cause the measured display portion 90 to match, or follow the target display portion 94.

Figure 4A:
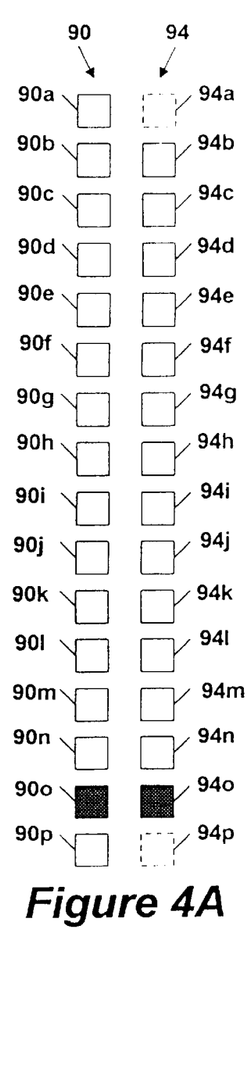
FIGS. 4A, 4B, 4C, 4D and 4E illustrate exemplary states of the display of FIG. 4 in operation.
Figure 4B:
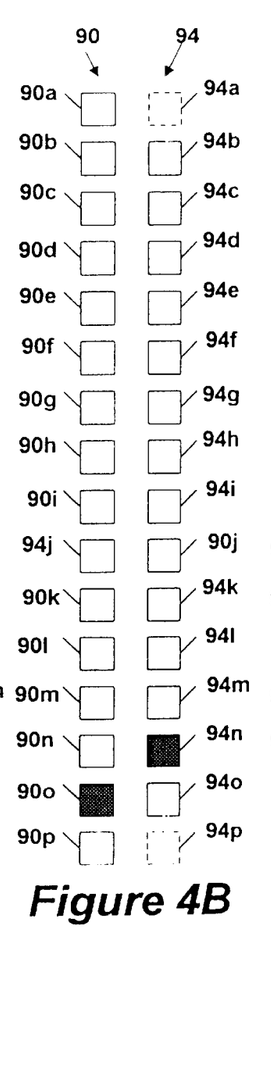
Figure 4C:
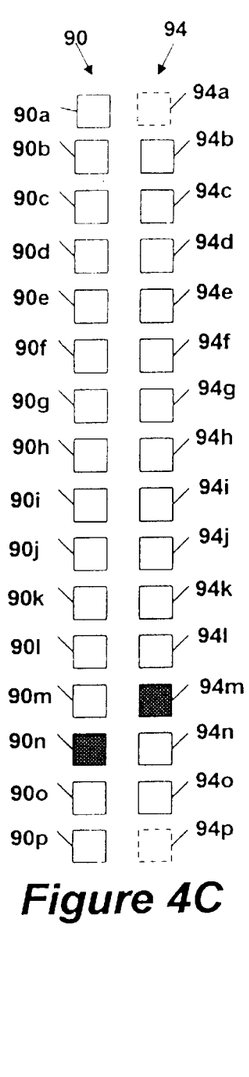
Figure 4D:
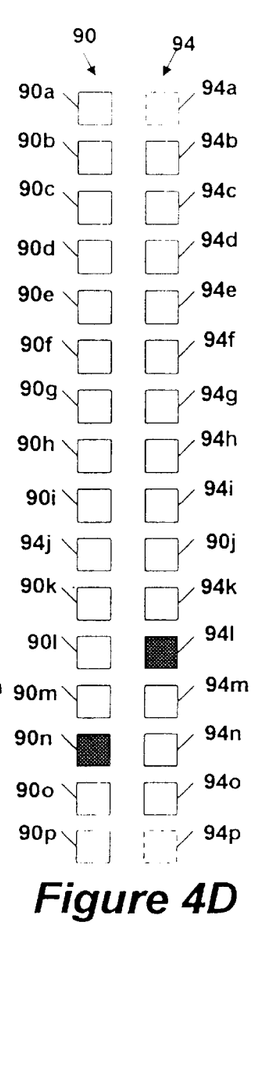
Figure 4E:
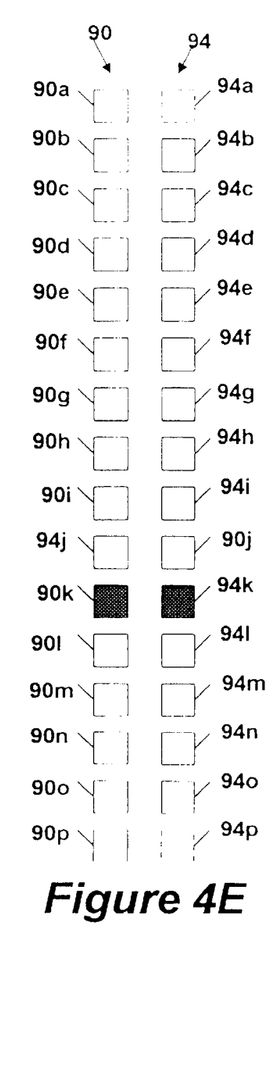

FIGS. 4A–4E illustrate examples of various states of the display portions 90 and 94 during operation. The progression of FIGS. 4A–4E illustrates a target inspiration volume pattern in the form of a sine wave function shown on target display portion 94. In FIG. 4A, the target inspiration volume is indicated by illuminated LED 94o and the patient's actual inspiration volume matches the target volume since the horizontally aligned LED 90o is illuminated. In each of FIGS. 4B–4D, the discrepancy between the illuminated measured inspiration volume LED and the illuminated target inspiration volume LED indicates that the patient should increase his or her inspiration volume to comply with the target breathing pattern. In FIG. 4E, the patient's inspiration volume has caught up to, and matches the target inspiration volume since the measured inspiration volume LED 90k is illuminated when the horizontally aligned target inspiration volume LED 94k is illuminated.

Figure 5:
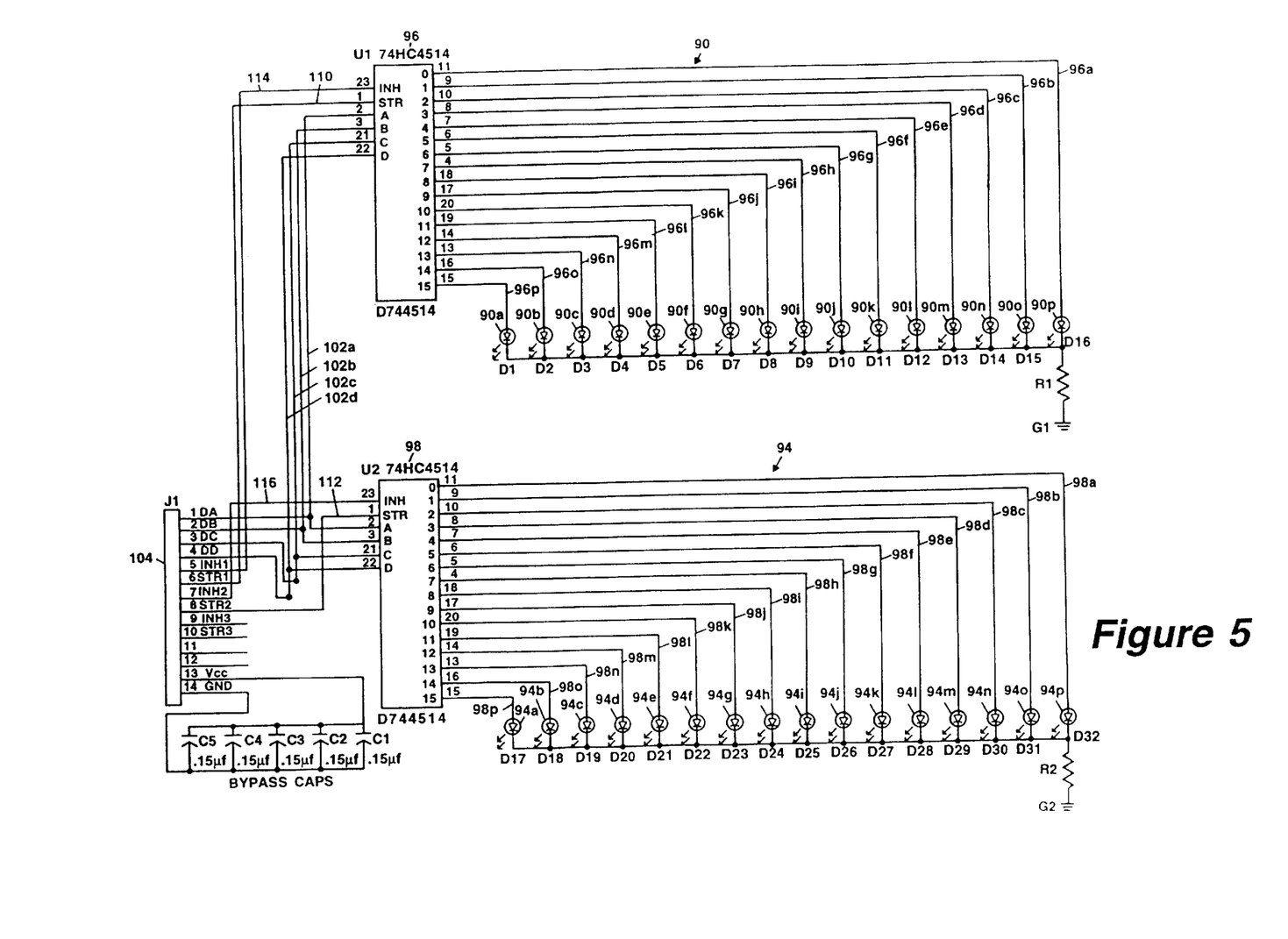
FIG. 5 is a schematic of the display of FIG. 4.

Referring to FIG. 5, each display portion 90, 94 includes a respective demultiplexer 96, 98 which is responsive to four data input signals 102a, 102b, 102c and 102d for providing digital output signals on signal lines 96a–96p, 98b–98o in order to illuminate an appropriate one of the LEDs 90a–90p, 94b–94o, respectively. In the illustrative embodiment, the demultiplexers 96, 98 are of the type sold by National Semiconductor of Santa Clara, Calif. under the product number 74HC4514. The processor 14 provides the four data input signals 102a–102d to each of the demultiplexers 96, 98 via the digital I/O board 21 (FIG. 1) which is coupled to a connector 104.

Each LED 90a–90p, 94a–94p is coupled between an output signal line of the respective demultiplexer 96, 98 and through a current limiting resistor to ground. More particularly, LEDs 90a–90p are coupled between output signal lines 96a–96p of demultiplexer 96 and LEDs 94a–94p are coupled between output signal lines 98a–98p of demultiplexer 98, respectively. Thus, when the demultiplexer output signal on the respective signal line goes high, the corresponding LED is illuminated.

Also provided by the processor 14 to each of the demultiplexers 96, 98 via the digital I/O board 21 and connector 104 is a strobe signal 110, 112 and an inhibit signal 114, 116, respectively. The strobe signals 110, 112 control latching of the data input signals 102a–102d by the respective demultiplexer 96, 98. More particularly, a positive-going pulse on a strobe signal line causes the respective demultiplexer to capture, or latch in the data input signals and to provide output signals according to the following Table:

| Signal Line 102a | Signal Line 102b | Signal Line 102c | Signal Line 102d | Illuminated LED when strobe 110 high | Illuminated LED when. strobe 112 high |
|---|---|---|---|---|---|
| 0 | 0 | 0 | 0 | 90p | |
| 0 | 0 | 0 | 1 | 90o | 94o |
| 0 | 0 | 1 | 0 | 90n | 94n |
| 0 | 0 | 1 | 1 | 90m | 94m |
| 0 | 1 | 0 | 0 | 90l | 94l |
| 0 | 1 | 0 | 1 | 90k | 94k |
| 0 | 1 | 1 | 0 | 90j | 94j |
| 0 | 1 | 1 | 1 | 90i | 94i |
| 1 | 0 | 0 | 0 | 90h | 94h |
| 1 | 0 | 0 | 1 | 90g | 94g |
| 1 | 0 | 1 | 0 | 90f | 94f |
| 1 | 0 | 1 | 1 | 90e | 94e |
| 1 | 1 | 0 | 0 | 90d | 94d |
| 1 | 1 | 0 | 1 | 90c | 94c |
| 1 | 1 | 1 | 0 | 90b | 94b |
| 1 | 1 | 1 | 1 | 90a | |

The inhibit signals 114, 116 are active-high signals for disabling the outputs of the demultiplexers 96, 98. When an inhibit signal 114, 116 is at a logic high level, all of the outputs of the respective demultiplexer are low, thereby turning off all of the respective LEDs. During certain stages of operation, it may be desirable to turn off one or both of the display portions 90, 94, such as when other features of the system 10 and display 18 are in use.

Figure 6:
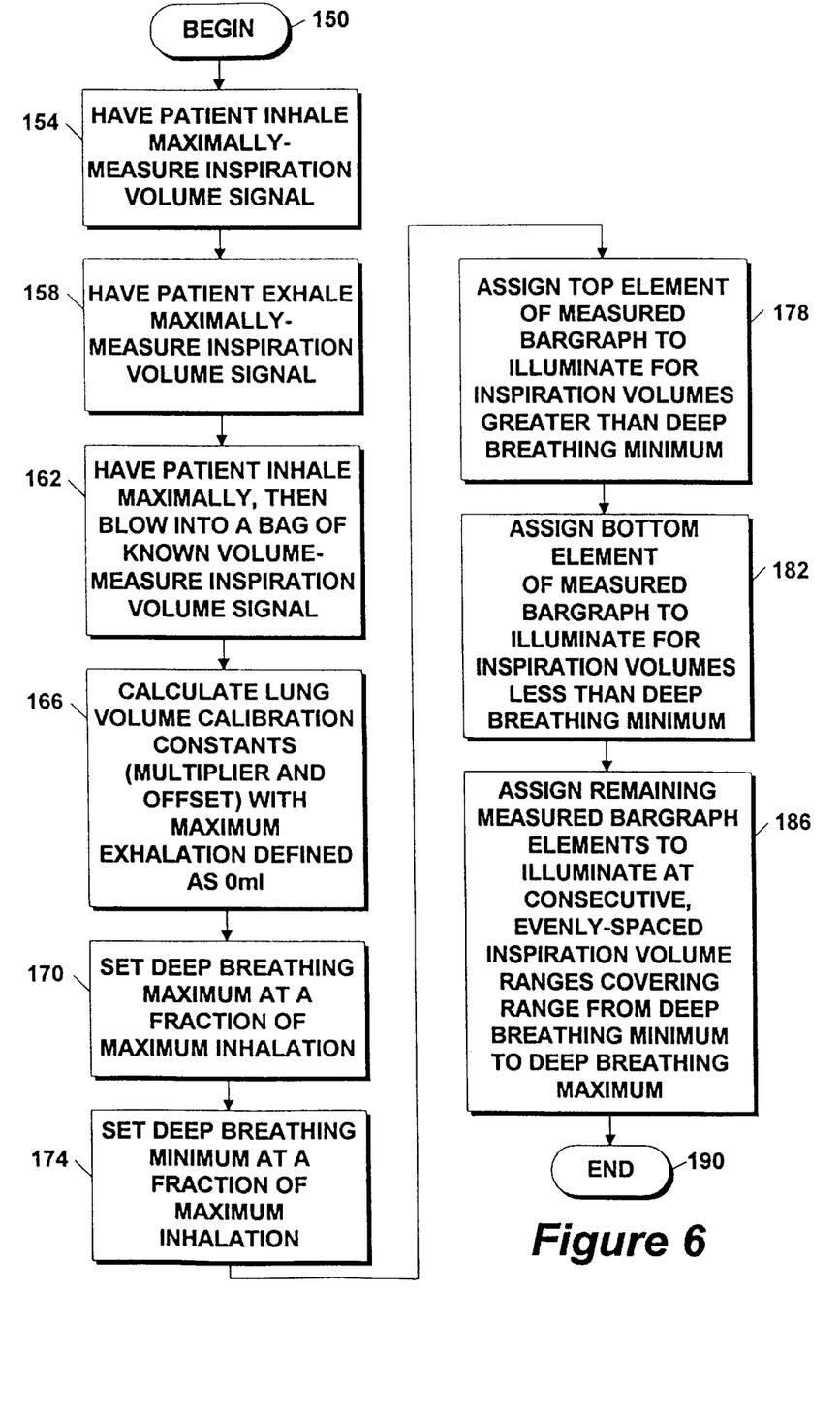
FIG. 6 is a flow diagram illustrating a method of calibrating the display of FIG. 4.

Referring to FIG. 6, a method of calibrating the display portions 90 and 94 commences in step 150, following which the patient, or subject is instructed to inhale as deeply as possible, to a maximal inhalation level in step 154. Also in step 154, the maximal inhalation level is measured by the inspiration volume amplifier 24 (FIG. 1) and the value of the output signal 34 is stored by the processor 14 in the memory 16. In subsequent step 158, the patient is instructed to exhale as deeply as possible, to a maximal exhalation level which is measured and stored in memory 16.

In step 162, the patient is instructed to inhale as deeply as possible and then to exhale into a bag of known volume, such as 800 mL, following which the inspiration volume amplifier 24 measures the patient's inspiration volume. This inspiration volume measurement thus provides a data point at which the measured inspiration volume is known to have a value equal to the maximal inhalation level minus the volume of the bag.

In step 166, the processor 14 calculates lung volume calibration constants for the patient, which include multiplier and offset constants used to convert the digital version 34 of the amplifier output signal 26 into a physical measure of the patient's inspiration volume, such as milliliters.

The calibration multiplier is determined in response to steps 154 and 162. The difference between the value of the digital version 34 of the amplifier signal 26 in steps 154 and 162 corresponds to the known volume of the bag. Thus, the number of milliliters represented by each voltage gradation is computed by setting the voltage difference between the inspiration volume signal measured in step 162 and the inspiration volume signal measured in step 154 equal to the volume of the bag, such as 800 mL.

In the illustrative embodiment, the maximum exhalation level is defined as zero milliliters. The offset constant is selected so that when it is added to the product of the voltage measured in step 158 and the calibration multiplier, it results in zero milliliters.

Having determined the subject's maximum inhalation volume and maximum exhalation volume, in process step 170, a predetermined fraction of the maximum inhalation volume is computed to define a deep breathing maximum. In the illustrative embodiment, the deep breathing maximum is approximately 85% of the patient's maximum inhalation volume. Similarly, in step 174, a predetermined fraction of the patient's maximum inhalation volume is computed and defines a deep breathing minimum. In the illustrative embodiment, the deep breathing minimum is 15% of the patient's maximum inhalation volume.

In step 178, the top LED 90a of the measured inspiration volume display portion 90 is assigned to illuminate whenever the measured inspiration volume exceeds the deep breathing maximum. Similarly, in step 182, the bottom LED 90p is assigned to illuminate whenever the measured inspiration volume is less than the deep breathing minimum.

Thereafter, in step 186, the range of inspiration volume represented by each of the remaining display elements 90b–90o and 94b–94o of the display portions 90, 94, respectively, is determined. To this end, the total volume between the deep breathing maximum and the deep breathing minimum is divided by the number of display devices, following which the calibration process terminates in step 190. For example, consider the case where the patient's deep breathing minimum is 150 mL and the deep breathing maximum is 850 mL. In this case, each of LEDs 90b–90o and 94b–94o represents approximately 50 mL of inspiration volume.

Figure 7:
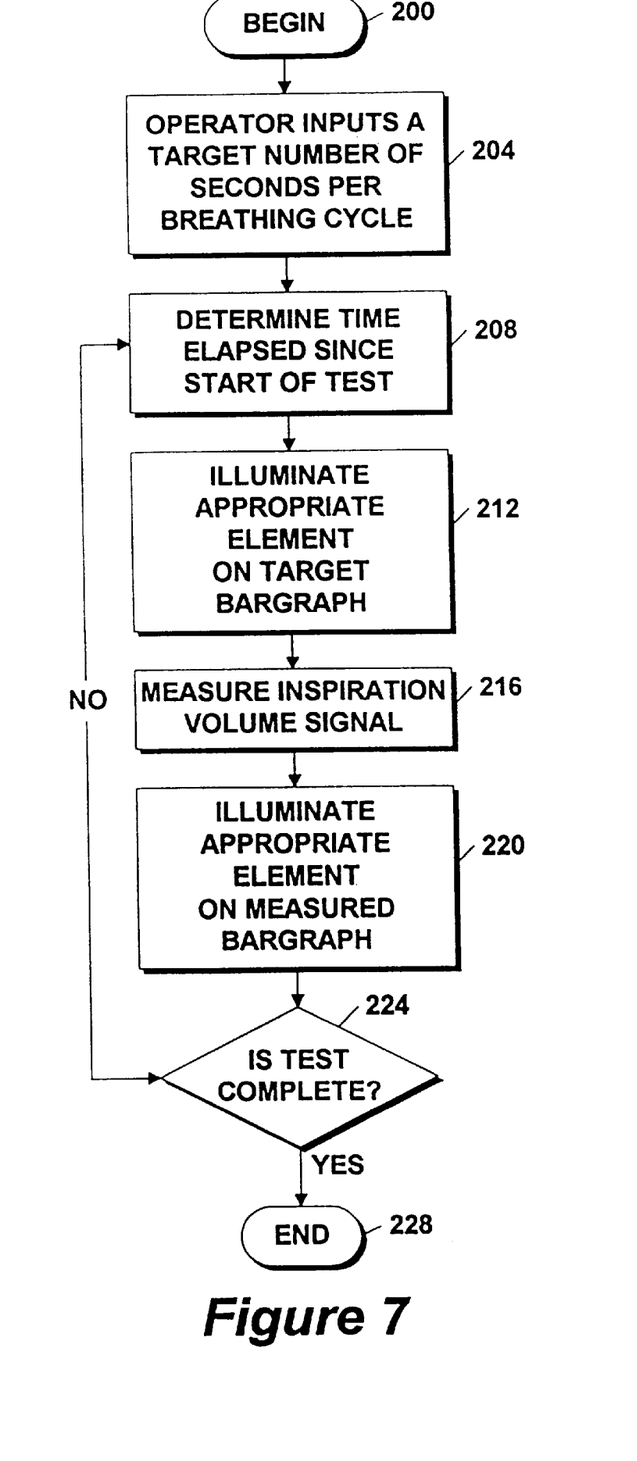
FIG. 7 is a flow diagram illustrating a method of operation of the system of FIG. 1.

Referring to FIG. 7, a method of operation of the processor 14 in driving the display portions 90 and 94 commences in step 200, following which the operator or user of the system enters a target breathing rate (i.e., a desired number of seconds per breathing cycle). As noted above, a typical target rate useful in neuropathy diagnosis is on the order of ten seconds per breathing cycle.

In step 208, the processor 14 determines how many seconds have lapsed since the beginning of the particular test. Thereafter, in step 212, the appropriate LED 94b–94o on the target display portion 94 is illuminated. In the illustrative embodiment, the target display portion 94 is controlled in accordance with a sine wave function and, specifically, according to the following equation:

$$(N - 2 - 0.5)\sin\left(\frac{2\Pi \cdot \text{target breathing rate}}{\text{elapsed time}}\right) + (N - 2 + 0.5)$$

where N is the number of utilized LEDs 94b–94o of the target display portion. The integer portion of the result of the above equation indicates the number of the LED that is activated (i.e., where LED 94o is LED one, LED 94n is LED two, etc.). The processor 14 activates the appropriate LED by providing the data input signals 102a–102d at the appropriate logic levels according to the Table above and the lung volume range assigned to each LED 94b–94o in calibration steps 186 (FIG. 6) and by providing a positive-going pulse on the strobe signal line 112 to the demultiplexer 98 (FIG. 5).

Once the appropriate LED on the target inspiration volume display portion 94 is illuminated, the actual inspiration volume is measured by sampling the amplifier output signal 34 (FIG. 1) in step 216. Thereafter, in step 220, the processor 14 activates the appropriate LED on the measured display portion 90 in accordance with the value of the digital signal 34, the lung volume range assigned to each LED 90a–90p in calibration steps 178, 182 and 186 (FIG. 6) and the Table provided above.

In subsequent step 224, it is determined whether the test is complete. Typically, the patient's inspiration volume is measured over a predetermined interval measured by a timer associated with the processor 14. If the test is not yet complete, then the process is repeated starting at step 208. Alternatively, the process is terminated in step 228.

Having described the preferred embodiments of the invention, it will now become apparent to one of ordinary skill in the art that other embodiments incorporating their concepts may be used. For example, in applications in which multiple loops 28, 28' (FIG. 1) are used, multiple respective amplifier circuits, like circuit 24 of FIG. 3, may be used to individually measure the respective inductance. Further, the output of such amplifiers may be weighted according to the position of the respective loop relative to the patient's lungs.

Further, it will be appreciated by those of ordinary skill in the art that techniques and apparatus for measuring inspiration volume other than that particularly described herein may be used in conjunction with the patient compliance apparatus and techniques described herein. For example, an airflow meter including an airflow tube may be used to measure a patient's inspiration volume and provide an inspiration volume signal displayed in association with a target inspiration volume as described herein.

It is felt therefore that these embodiments should not be limited to disclosed embodiments but rather should be limited only by the spirit and scope of the appended claims. All publications and references cited herein are expressly incorporated herein by reference in their entirety.

What is claimed is:

1. A system for improving patient compliance with a predetermined breathing pattern during inspiration volume measurements, comprising:
    an inspiration volume amplifier for measuring the inspiration volume of a patient for heart rate variability analysis;
    a display comprising:
        a first display portion for displaying the measured inspiration volume of the patient; and
        a second display portion disposed adjacent to the first display portion for displaying a target inspiration volume; and
    a processor responsive to the measured inspiration volume of the patient for controlling the first display portion, wherein the processor is operative to control the second display portion in accordance with a predetermined mathematical function.

2. The system of claim 1, wherein the inspiration volume amplifier is adapted for coupling to a conductive loop suitable for positioning around and conforming to the patient's chest.

3. The system of claim 2, wherein the inspiration volume amplifier comprises a delay measuring circuit for measuring a delay between a square-wave signal applied to a first terminal of the conductive loop and a signal at a second terminal of the conductive loop.

4. The system of claim 1, wherein the first and second display portions are in the form of bar graphs.

5. The system of claim 1, wherein each of the first and second display portions comprises a plurality of LEDs.

6. The system of claim 1, wherein the first display portion comprises a demultiplexer responsive to a plurality of data input signals provided by the processor for controlling the first display portion and the second display portion comprises a demultiplexer responsive to the plurality of data input signals provided by the processor for controlling the second display portion.

7. The system of claim 1, wherein the predetermined mathematical function is a sine wave function.

8. The system of claim 1, wherein the predetermined mathematical function is a chirp function.

9. A system for improving patient compliance with a predetermined breathing pattern during inspiration volume measurements comprising:
    an inspiration volume amplifier for measuring the inspiration volume of a patient, said inspiration volume amplifier adapted for coupling to a conductive loop suitable for positioning around and conforming to the patient's chest and comprising a delay measuring circuit for measuring a delay between a square-wave signal applied to a first terminal of the conductive loop and a signal at a second terminal of the conductive loop;
    a display comprising:
        a first display portion for displaying the measured inspiration volume of the patient; and
        a second display portion disposed adjacent to the first display portion for displaying a target inspiration volume; and
    a processor responsive to the measured inspiration volume of the patient for controlling the first display portion, wherein the processor is operative to control the second display portion in accordance with a predetermined function.

10. A system for improving patient compliance with a predetermined breathing pattern during inspiration volume measurements comprising:
    an inspiration volume amplifier for measuring the inspiration volume of a patient;
    a display comprising:
        a first display portion for displaying the measured inspiration volume of the patient, said first display portion comprising a demultiplexer responsive to a plurality of data input signals provided by the processor for controlling the first display portion; and
        a second display portion disposed adjacent to the first display portion for displaying a target inspiration volume, said second display portion comprising a demultiplexer responsive to the plurality of data input signals provided by the processor for controlling the second display portion; and
    a processor responsive to the measured inspiration volume of the patient for controlling the first display portion, wherein the processor is operative to control the second display portion in accordance with a predetermined function.

11. A system for improving patient compliance with a predetermined breathing pattern comprising:
    (a) a device for measuring the inspiration volume of a patient;
    (b) a display for displaying the measured inspiration volume of the patient, wherein said display comprises:
        (i) a deep breathing maximum display portion for indicating when the patient's breathing exceeds a deep breathing maximum level, wherein said deep breathing maximum level is a function of said measured inspiration volume of the patient; and
        (ii) a deep breathing minimum display portion for indicating when the patient's breathing falls below a deep breathing minimum level, wherein said deep breathing minimum level is a function of said measured inspiration volume of the patient; and (c) a processor for controlling said display in accordance with the measured inspiration volume of the patient.

12. The system of claim 11, wherein said display further comprises a target inspiration volume portion for displaying a target inspiration volume.

13. The system of claim 12, wherein said processor controls said target inspiration volume portion according to a predetermined mathematical function.

14. A method for improving patient compliance with a predetermined breathing pattern during inspiration volume measurements, comprising the steps of:

measuring the patient's inspiration volume;

computing a deep breathing maximum level as a function of the patient's measured inspiration volume and a deep breathing minimum level as a function of the patient's measured inspiration volume;

displaying the measured inspiration volume of the patient, including when said measured inspiration volume is greater than said deep breathing maximum level and when said measured inspiration volume is less than said deep breathing minimum level;

displaying a target inspiration volume in accordance with a predetermined function; and instructing the patient to breathe in a manner that causes the measured inspiration volume display to match the target inspiration volume display.

* * * * *

UNITED STATES PATENT AND TRADEMARK OFFICE
CERTIFICATE OF CORRECTION

PATENT NO : 6,106,481
DATED : August 22, 2000
INVENTOR(S) : Alan M. Cohen

It is certified that error appears in the above-identified patent and that said Letters Patent are hereby corrected as shown below:

Front page, under Inventor Section [75], delete "Arlington" and replace with --Newton--.

Col. 7, line 67, before "display" insert --to--.

Signed and Sealed this

Fifteenth Day of May, 2001

NICHOLAS P. GODICI

*Attest:*

*Attesting Officer*   *Acting Director of the United States Patent and Trademark Office*